(12) United States Patent
Leven

(10) Patent No.: US 9,636,498 B2
(45) Date of Patent: May 2, 2017

(54) LEAD ANCHOR WITH A WEDGE AND SYSTEMS USING THE LEAD ANCHOR

(71) Applicant: Boston Scientific Neuromodulation Corporation, Valencia, CA (US)

(72) Inventor: Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/225,664

(22) Filed: Aug. 1, 2016

(65) Prior Publication Data

US 2017/0036013 A1 Feb. 9, 2017

Related U.S. Application Data

(60) Provisional application No. 62/200,582, filed on Aug. 3, 2015.

(51) Int. Cl.
*A61N 1/05* (2006.01)
(52) U.S. Cl.
CPC ............ *A61N 1/0558* (2013.01); *A61N 1/05* (2013.01); *A61N 1/0539* (2013.01)
(58) Field of Classification Search
None
See application file for complete search history.

(56) References Cited

U.S. PATENT DOCUMENTS

| | | |
|---|---|---|
| 376,810 A | 1/1888 | Brill |
| 612,665 A | 10/1898 | Thorp et al. |
| 2,046,837 A | 7/1936 | Phillips |
| 3,866,615 A | 2/1975 | Hewson |
| 4,141,752 A | 2/1979 | Shipko |
| 4,276,882 A | 7/1981 | Dickhudt et al. |
| 4,316,471 A | 2/1982 | Shipko et al. |
| 4,462,401 A | 7/1984 | Burgio |
| 4,632,670 A | 12/1986 | Mueller, Jr. |
| 4,764,132 A | 8/1988 | Stutz, Jr. |
| 4,858,623 A | 8/1989 | Bradshaw et al. |
| 5,036,862 A | 8/1991 | Pohndorf |
| 5,107,856 A | 4/1992 | Kristiansen et al. |

(Continued)

FOREIGN PATENT DOCUMENTS

| | | |
|---|---|---|
| EP | 85417 A1 | 8/1983 |
| EP | 0597213 A1 | 5/1994 |

(Continued)

*Primary Examiner* — Brian T Gedeon
(74) *Attorney, Agent, or Firm* — Lowe Graham Jones PLLC; Bruce E. Black

(57) ABSTRACT

A lead anchor includes an anchor body having a first end, a second end, at least one least one lateral portion, and a medial portion. The anchor body defines at least one lead channel extending longitudinally from the first end to the second end. A wedge element is disposed adjacent to at least a portion of the at least one lead channel and is configured and arranged to move between an open position and an engagement position. In the engagement position, the wedge element engages a lead disposed in the at least one lead channel to hold the lead within the lead anchor, and in the open position, the wedge releases the lead to move relative to or be released from the lead anchor. The lead anchor further includes an actuator configured and arranged to move the wedge element from the open position to the engagement position.

20 Claims, 10 Drawing Sheets

(56) References Cited

U.S. PATENT DOCUMENTS

| | | |
|---|---|---|
| 5,158,097 A | 10/1992 | Christlieb |
| 5,228,248 A | 7/1993 | Haddock |
| 5,269,809 A | 12/1993 | Hayhurst et al. |
| 5,370,662 A | 12/1994 | Stone et al. |
| 5,376,108 A | 12/1994 | Collins et al. |
| 5,484,445 A | 1/1996 | Knuth |
| 5,584,874 A | 12/1996 | Rugland et al. |
| 5,628,780 A | 5/1997 | Helland et al. |
| 5,746,722 A | 5/1998 | Pohndorf et al. |
| 5,865,843 A | 2/1999 | Baudino |
| 5,895,360 A | 4/1999 | Christopherson et al. |
| 5,957,968 A | 9/1999 | Belden et al. |
| 6,181,969 B1 | 1/2001 | Gord |
| 6,192,279 B1 | 2/2001 | Barreras, Sr. et al. |
| 6,360,750 B1 | 3/2002 | Gerber et al. |
| 6,473,654 B1 | 10/2002 | Chinn |
| 6,516,227 B1 | 2/2003 | Meadows et al. |
| 6,606,523 B1 | 8/2003 | Jenkins |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,901,287 B2 | 5/2005 | Davis et al. |
| 6,978,180 B2 | 12/2005 | Tadlock |
| 6,984,145 B1 | 1/2006 | Lim |
| 7,069,083 B2 | 6/2006 | Finch et al. |
| 7,072,719 B2 | 7/2006 | Vinup et al. |
| 7,161,461 B1 | 1/2007 | Nelson |
| 7,184,841 B1 | 2/2007 | Bodner et al. |
| 7,235,078 B2 | 6/2007 | West, Jr. |
| 7,244,150 B1 | 7/2007 | Brase et al. |
| 7,343,202 B2 | 3/2008 | Mrva et al. |
| 7,402,076 B1 | 7/2008 | Lim |
| 7,437,193 B2 | 10/2008 | Parramon et al. |
| 7,447,546 B2 | 11/2008 | Kim et al. |
| 7,610,102 B2 | 10/2009 | Kowalczyk |
| 7,672,734 B2 | 3/2010 | Anderson et al. |
| 7,761,165 B1 | 7/2010 | He et al. |
| 7,787,960 B2 | 8/2010 | Lubenow |
| 7,848,803 B1 | 12/2010 | Jaax et al. |
| 7,853,321 B2 | 12/2010 | Jaax et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,224,451 B2 | 7/2012 | Jaax et al. |
| 8,229,573 B2 | 7/2012 | Chen et al. |
| 8,315,704 B2 | 11/2012 | Jaax et al. |
| 8,364,278 B2 | 1/2013 | Pianca et al. |
| 8,568,462 B2 | 10/2013 | Sixto et al. |
| 2001/0000187 A1 | 4/2001 | Peckham et al. |
| 2002/0107554 A1 | 8/2002 | Biggs et al. |
| 2003/0074023 A1 | 4/2003 | Kaplan et al. |
| 2003/0078623 A1 | 4/2003 | Weinberg et al. |
| 2003/0208247 A1 | 11/2003 | Spinelli et al. |
| 2004/0059392 A1 | 3/2004 | Parramon et al. |
| 2005/0033393 A1 | 2/2005 | Daglow |
| 2005/0165465 A1 | 7/2005 | Pianca et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0173520 A1 | 8/2006 | Olson |
| 2006/0205995 A1 | 9/2006 | Browning |
| 2006/0206162 A1 | 9/2006 | Wahlstrand et al. |
| 2007/0010794 A1 | 1/2007 | Dann et al. |
| 2007/0050005 A1 | 3/2007 | Lauro |
| 2007/0078399 A1 | 4/2007 | Olson |
| 2007/0100348 A1 | 5/2007 | Cauthen et al. |
| 2007/0150036 A1 | 6/2007 | Anderson |
| 2007/0219595 A1 | 9/2007 | He |
| 2007/0255369 A1 | 11/2007 | Bonde et al. |
| 2008/0071320 A1 | 3/2008 | Brase |
| 2008/0091255 A1 | 4/2008 | Caparso et al. |
| 2008/0140130 A1 | 6/2008 | Chan et al. |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0228251 A1 | 9/2008 | Hill |
| 2008/0243220 A1 | 10/2008 | Barker |
| 2008/0275401 A1 | 11/2008 | Sage et al. |
| 2008/0312712 A1 | 12/2008 | Penner |
| 2009/0018601 A1 | 1/2009 | Deininger et al. |
| 2009/0112272 A1 | 4/2009 | Schleicher et al. |
| 2009/0198312 A1 | 8/2009 | Barker |
| 2009/0210043 A1 | 8/2009 | Reddy |
| 2009/0254151 A1 | 10/2009 | Anderson et al. |
| 2009/0259260 A1 | 10/2009 | Bentley et al. |
| 2009/0270940 A1 | 10/2009 | Deininger |
| 2009/0281571 A1 | 11/2009 | Weaver et al. |
| 2009/0281576 A1 | 11/2009 | Weaver et al. |
| 2009/0281579 A1 | 11/2009 | Weaver et al. |
| 2010/0094425 A1 | 4/2010 | Bentley et al. |
| 2010/0174240 A1 | 7/2010 | Wells et al. |
| 2010/0274336 A1 | 10/2010 | Nguyen-Stella et al. |
| 2010/0286670 A1 | 11/2010 | Doyle et al. |
| 2010/0312319 A1 | 12/2010 | Barker |
| 2011/0022066 A1 | 1/2011 | Sevrain |
| 2011/0022142 A1 | 1/2011 | Barker et al. |
| 2011/0060395 A1 | 3/2011 | Cantlon |
| 2011/0178573 A1 | 7/2011 | Nguyen-Stella et al. |
| 2011/0264180 A1 | 10/2011 | Hamilton |
| 2012/0150202 A1 | 6/2012 | Chen et al. |
| 2012/0185027 A1 | 7/2012 | Pianca et al. |
| 2012/0232626 A1 | 9/2012 | Daglow |
| 2012/0277670 A1 | 11/2012 | Goetz |
| 2012/0283835 A1 | 11/2012 | Bentley et al. |
| 2012/0330355 A1 | 12/2012 | Finley et al. |
| 2013/0149031 A1 | 6/2013 | Changsrivong |
| 2013/0204336 A1 | 8/2013 | Sharma |
| 2013/0238023 A1 | 9/2013 | Wales et al. |
| 2014/0074093 A9 | 3/2014 | Nelson et al. |
| 2014/0180345 A1 | 6/2014 | Chan et al. |
| 2014/0343645 A1 | 11/2014 | Wechter |
| 2015/0005856 A1 | 1/2015 | Pianca et al. |
| 2015/0045865 A1 | 2/2015 | Nagen et al. |
| 2015/0051674 A1 | 2/2015 | Barner et al. |
| 2015/0051675 A1 | 2/2015 | Barner |
| 2015/0066121 A1 | 3/2015 | Govea et al. |
| 2015/0246216 A1 | 9/2015 | Barker |

FOREIGN PATENT DOCUMENTS

| | | |
|---|---|---|
| JP | H07-014681 | 3/1995 |
| JP | 2001339829 A | 12/2001 |
| WO | 98/33551 A1 | 8/1998 |
| WO | 99/53994 | 10/1999 |
| WO | 00/13743 A2 | 3/2000 |
| WO | 00/64535 | 11/2000 |
| WO | 2004/054655 | 7/2004 |
| WO | 2006/086363 A2 | 8/2006 |
| WO | 2007/056384 A2 | 5/2007 |
| WO | 2007/083108 A2 | 7/2007 |
| WO | 2007/149994 A2 | 12/2007 |
| WO | 2008101026 A1 | 6/2008 |
| WO | 2008/094789 A1 | 8/2008 |
| WO | 2008/121708 A2 | 10/2008 |
| WO | 2010/126853 A1 | 11/2010 |
| WO | 2012151356 A1 | 11/2012 |
| WO | 2013112920 A1 | 8/2013 |

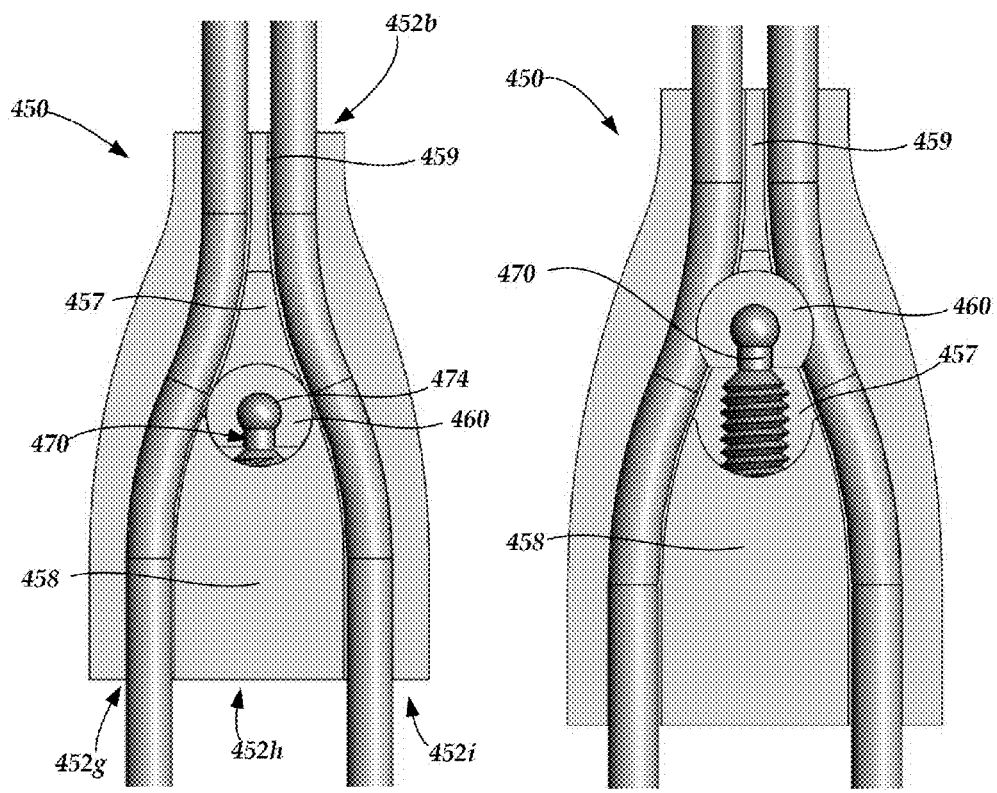

LEAD ANCHOR WITH A WEDGE AND SYSTEMS USING THE LEAD ANCHOR

CROSS-REFERENCE TO RELATED APPLICATIONS

This application claims the benefit under 35 U.S.C. §119 (e) of U.S. Provisional Patent Application Ser. No. 62/200,582, filed Aug. 3, 2015, which is incorporated herein by reference.

FIELD

The present invention is directed to the area of implantable electrical stimulation systems and methods of making and using the systems. The present invention is also directed to lead anchors for implantable electrical stimulation leads, as well as systems and methods using the lead anchors and leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a lead anchor including an anchor body having a first end and a second end and defining at least one lead channel extending longitudinally from the first end to the second end; a wedge element disposed adjacent to at least a portion of the at least one lead channel, the wedge element configured and arranged to move between an open position and an engagement position; and an actuator to move the wedge element towards the second end from the open position to the engagement position. In the engagement position, the wedge element engages a lead disposed in the at least one lead channel to hold the lead within the lead anchor, and in the open position, the wedge releases the lead to move relative to or be released from the lead anchor.

In at least some embodiments, the at least one lead channel includes two nonlinear lead channels extending longitudinally from the first end to the second end. In at least some embodiments, the two nonlinear lead channels are mirror images of each other. In at least some embodiments, each of the at least one lead channel includes a curved portion.

In at least some embodiments, the actuator is rotatable to move the wedge element from the open position to the engagement position. In at least some embodiments, the actuator is a screw. In at least some embodiments, the actuator includes a pin. In at least some embodiments, the actuator is configured and arranged to reversibly move the wedge element between the open position and the engagement position.

In at least some embodiments, the lead channel is open along one surface of the anchor body to permit side loading of at least one lead into the lead anchor. In at least some embodiments, the wedge element is C-shaped. In at least some embodiments, the wedge element has an oblong shape or polygonal shape. In at least some embodiments, the wedge element includes at least one pivotable arm.

Another embodiment is a kit including at least one electrostimulation lead; and any of the lead anchors described above for receiving the at least one electrostimulation lead in the lead channel of the lead anchor. In at least some embodiments, the kit further includes a control module.

Yet another embodiment is a method of anchoring at least one electrostimulation lead that includes inserting a first electrostimulation lead into the at least one lead channel of any one of the lead anchors described above with the wedge element in the open position; and moving the wedge element towards the second end from the open position to the engagement position using the actuator to anchor the lead to the lead anchor.

In at least some embodiments, the at least one lead channel includes two nonlinear lead channels extending longitudinally from the first end to the second end and the method further includes inserting a second electrostimulation lead into a different one of the at least one lead channel of the lead anchor with the wedge element in the open position.

In at least some embodiments, the method further includes attaching the lead anchor to patient tissue. In at least some embodiments, inserting a first electrostimulation lead includes side loading the first electrostimulation lead into the at least one lead channel of the lead anchor. In at least some embodiments, inserting a first electrostimulation lead includes end loading the first electrostimulation lead into the at least one lead channel of the lead anchor. In at least some embodiments, the method further includes coupling the first electrostimulation lead to a control module.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5A is a schematic top plan view of the lead anchor of FIG. 4A with the wedge element in an open position, according to the invention;

FIG. 5B is a schematic top plan view of the lead anchor of FIG. 4A, with the wedge element in an engagement position, according to the invention;

DETAILED DESCRIPTION

The present invention is directed to the area of implantable electrical stimulation systems and methods of making and using the systems. The present invention is also directed to lead anchors for implantable electrical stimulation leads, as well as systems and methods using the lead anchors and leads.

Suitable implantable electrical stimulation systems include, but are not limited to, a least one lead with one or more electrodes disposed along a distal end of the lead and one or more terminals disposed along the one or more proximal ends of the lead.

Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734;7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent applications Ser. Nos. 12/177,823 and 13/750,725, all of which are incorporated by reference in their entirety.

Figure 1:
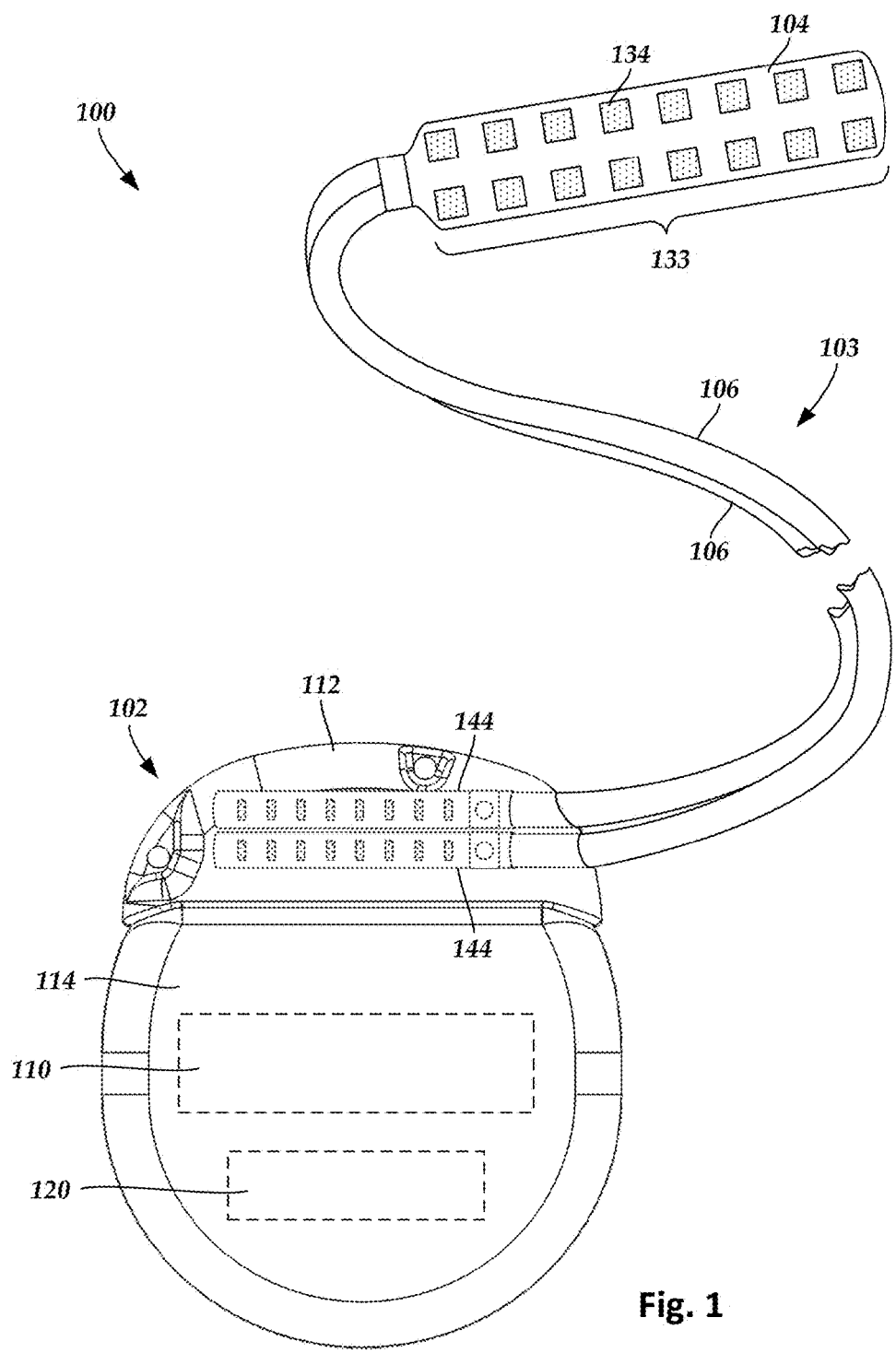
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
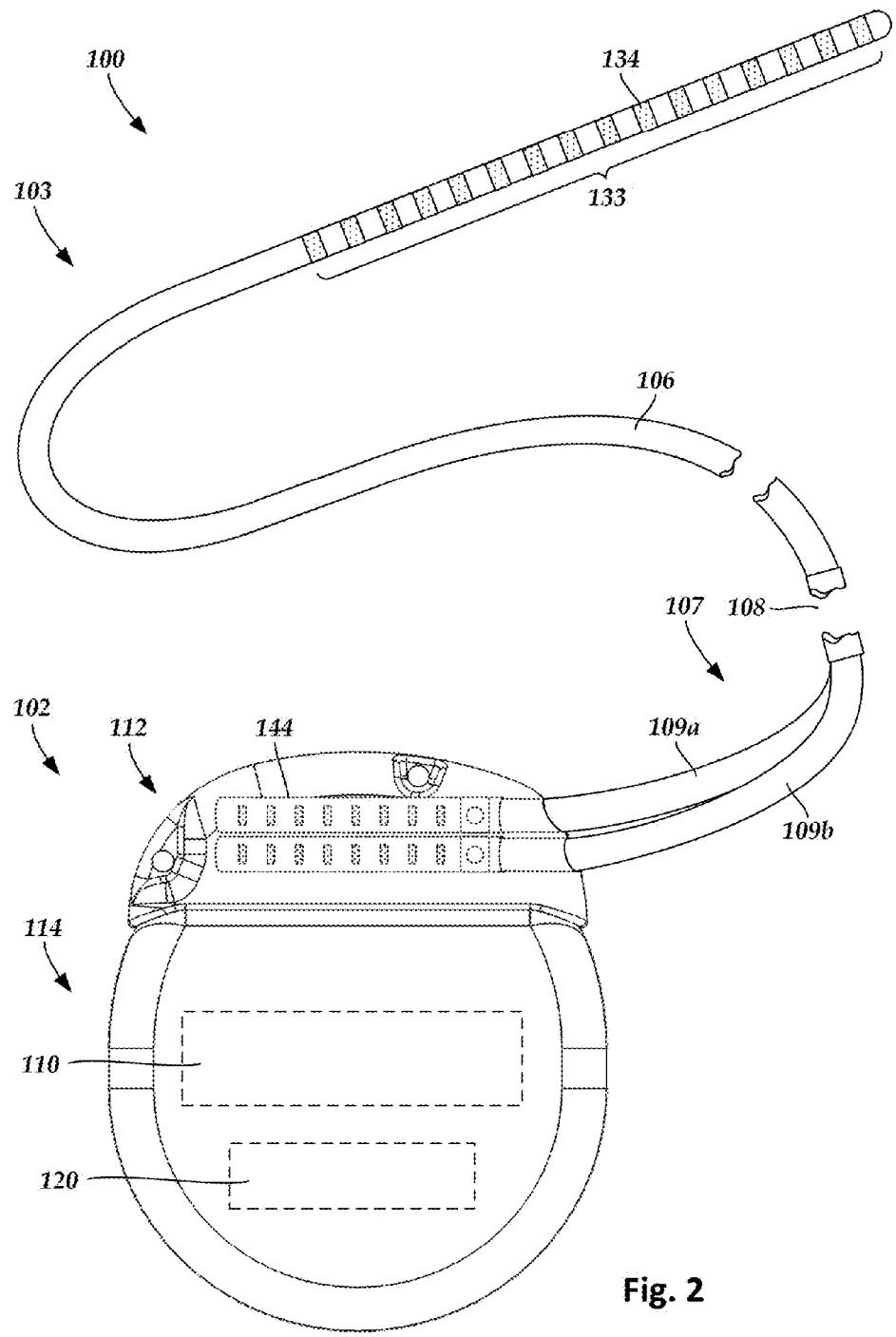
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
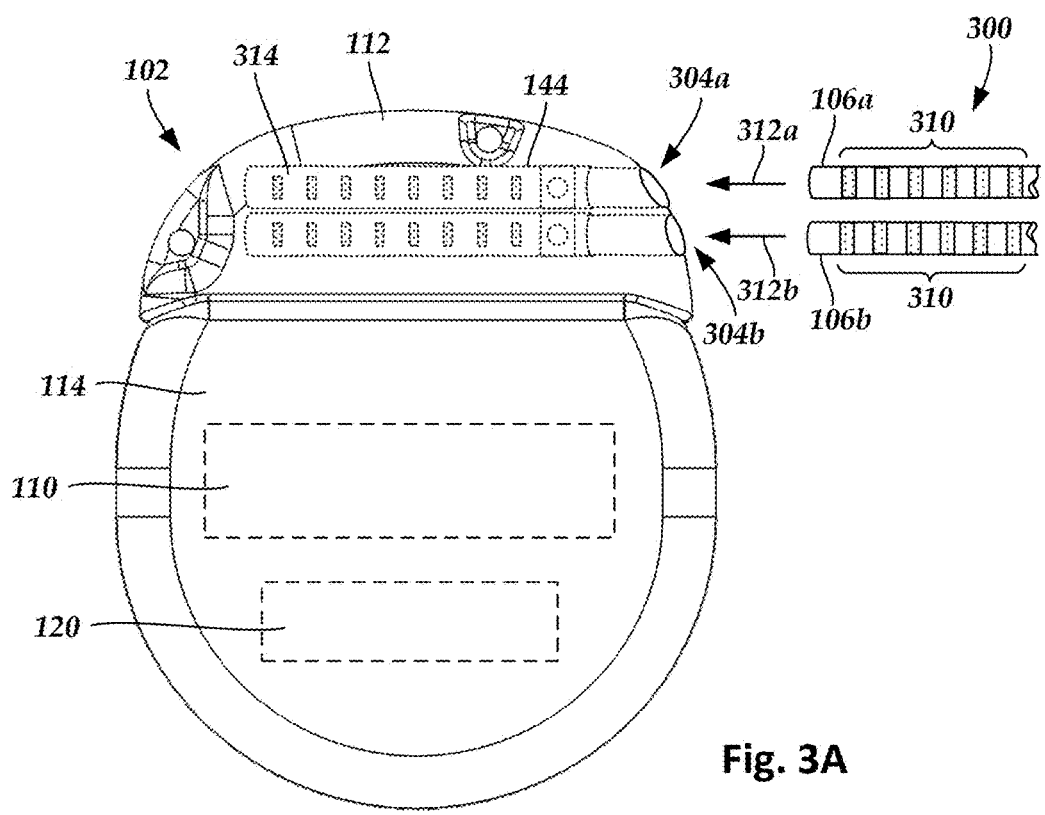
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated herein by reference in their entirety.

Figure 3B:
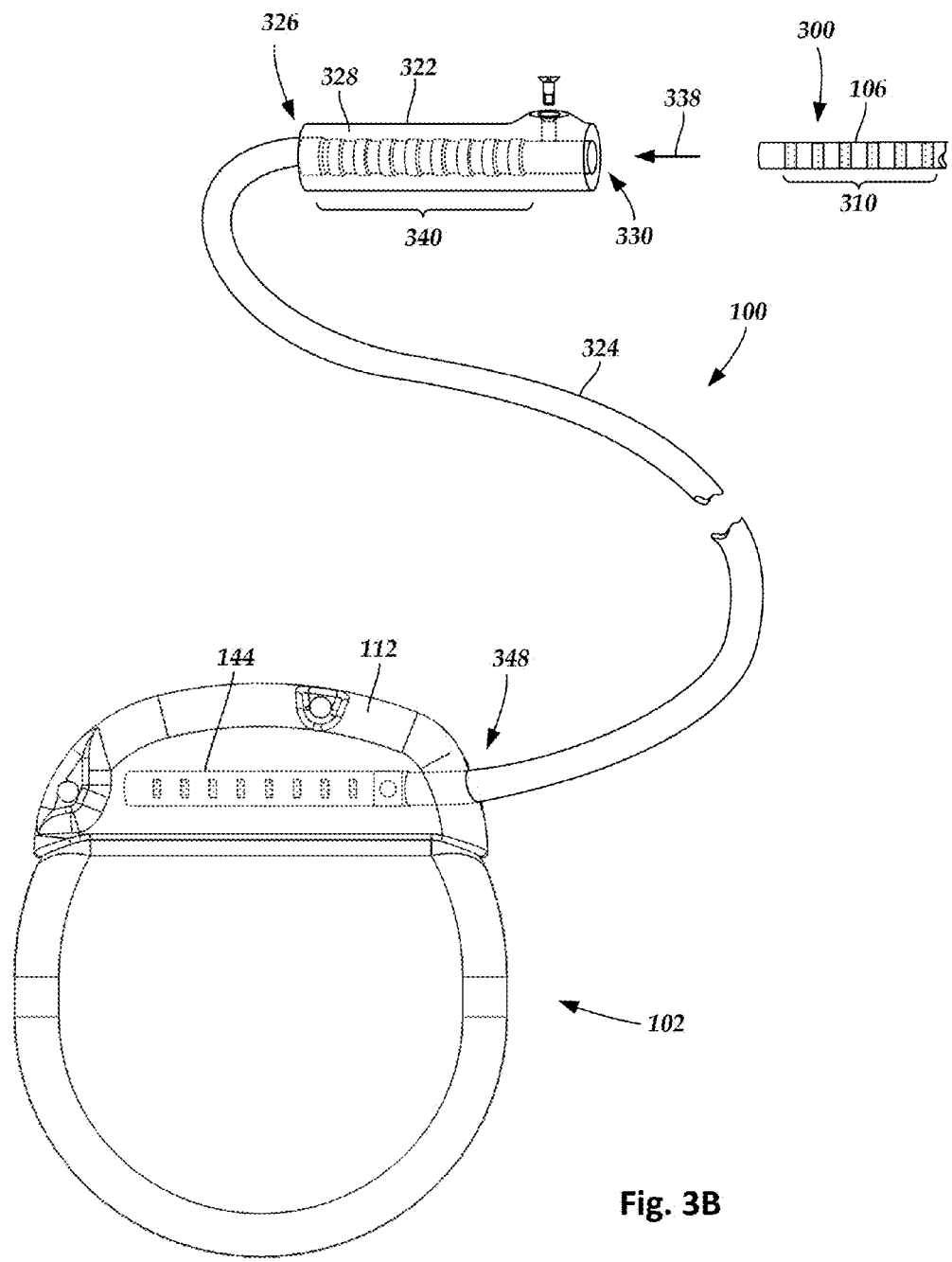
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

A lead can be anchored in patient tissue using a lead anchor. More particularly, a lead anchor can be designed to be end loaded, meaning that the lead anchor is slid onto the lead starting at either the proximal or distal end of the lead. Additionally or alternatively, a lead anchor can be designed so that the lead is side loaded into the lead anchor. Side loading involves inserting a portion of the lead body that is between the proximal and distal ends into the lead anchor from the top or bottom of the lead anchor. This is particularly advantageous for leads that are not isodiametric or which are bifurcated or branched. In such a lead, it may be difficult to slide a lead anchor along the lead. In at least some embodiments, the lead anchors disclosed herein permit both end loading and side loading of a lead into a lead channel of the lead anchor.

Figure 4A:
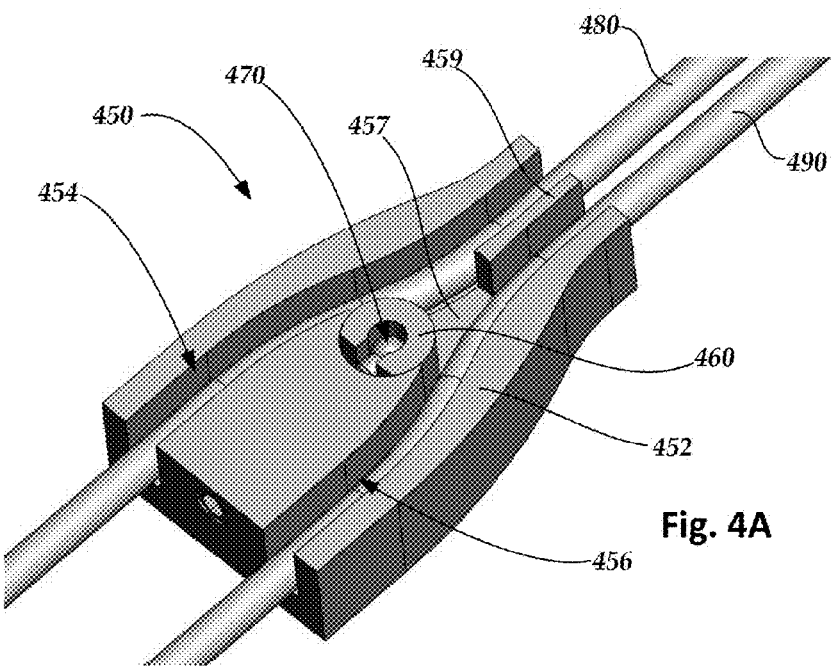
FIG. 4A is a schematic perspective view of one embodiment of a lead anchor, according to the invention, with the wedge element in an open position and leads disposed along channels of the lead anchor, according to the invention.

FIG. 4A is a schematic perspective view of one embodiment of a lead anchor 450 with two leads 480, 490 disposed therein. The lead anchor 450 has an anchor body 452 having a first end (see 452a in FIG. 4C) and a second end (see 452b in FIG. 4C). In at least some embodiments, the first end 452a and second end 452b of the anchor body 452 are defined so that the first end 452a of the anchor body 452 is closer to the clinician during an anchoring procedure and the second end 452b of the anchor body 452 is closer to the site of implantation or the target site for the leads 480, 490. Although the discussion herein will utilize this orientation of the lead anchor, it will be recognized, however, that the lead anchor can be reversed so that the first end 452a is closer to the site of implantation or the target site for the leads 480, 490 and the second end 452b is closer to the clinician during an anchoring procedure.

The anchor body 452 defines one or more lead channels 454, 456 along the length of the anchor body 452 from the first end 452a to the second end 452b. At the second end 452b of the anchor body 452, the leads 480, 490 follow exit paths defined by the lead channels 454, 456 and a medial divider 459. The one or more lead channels 454, 456 of the illustrated embodiment are nonlinear lead channels. In at least some embodiments, a nonlinear lead channel has one or more of a bend, a curve, or a corner; or any combination thereof. In at least some other embodiments, the one or more lead channels are linear lead channels that are angled toward each other towards the second end of the anchor body but, at least in some embodiments, do not converge with, or intersect, each other.

Figures 6A, 6B:
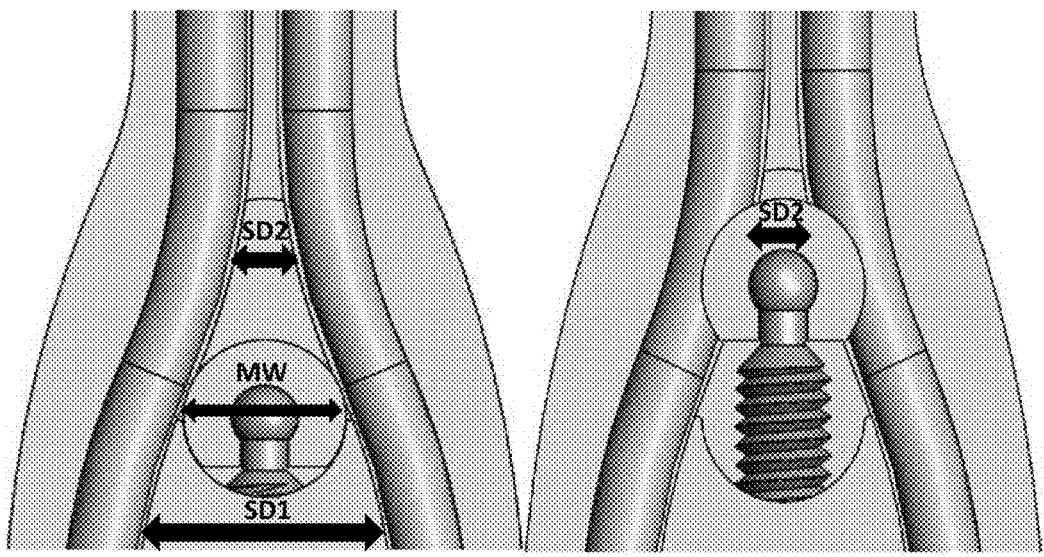
FIG. 6A is a schematic top plan detail view of the lead anchor of FIG. 5A, the lead anchor defining a first region, where the lead channels are separated by a first separation distance that is greater than the maximum width of the wedge element, and a second region, where the lead channels are separated by a second separation distance that is less than the maximum width of the wedge element, according to the invention.
FIG. 6B is a schematic top plan detail view of the lead anchor of FIG. 5B, where the wedge element is in an engagement position, where the lead channels are separated by a separation distance that is less than the maximum width of the wedge element, according to the invention.

The path of a lead channel along the anchor body 452 resists or prevents travel of a lead 480, 490 within the lead anchor 450 when the lead 480, 490 is disposed therein and a wedge element 460 engages the lead 480, 490 as described below. In at least some embodiments, the anchor body 452 defines a first region near the first end 452a of the anchor body 452, where the lead channels 454, 456 are separated by a first separation distance (SD1 in FIG. 6A) that is larger or wider than the maximum width (MW in FIG. 6A) of the wedge element, and a second region near the second end 452b of the anchor body 452, where the lead channels 454, 456 are separated by a second separation distance (SD2 in FIGS. 6A and 6B) that is smaller or narrower than the maximum width of the wedge element.

A lead anchor 450 may be configured and arranged to permit leads to be end loaded, side loaded, or both end loaded and side loaded. The lead channels 454, 456 may be defined along a top surface 452c (FIG. 4C) of the anchor body 452 that is open to permit both end loading and side loading of the lead anchor 450 onto the leads 480, 490. In at least some other embodiments, the anchor body 452 may permit end loading, but not side loading, of the leads 480, 490 into the lead anchor 450. For example, in at least some embodiments, the anchor body defines closed (or partially closed) top, bottom, and side surfaces and the lead channels are partially closed or are open only at the first 452a and second 452b ends to permit loading of the leads 480, 490 into the lead anchor.

The lead anchor 450 may be formed in the desired shape by any process including, for example, molding (including injection molding), casting, and the like. The lead anchor 450 may be formed of any biocompatible material such as, for example, silicone, polyurethane, polyetheretherketone ("PEEK"), epoxy, or a biocompatible metal or alloy, such as, for example, aluminum, nickel, titanium, nitinol, copper, gold, stainless steel, cobalt-chromium, or the like; or any combination thereof.

It will be appreciated that the material or materials forming the lead anchor 450 are sufficiently rigid to permit reception and anchoring of at least one lead in a patient. In some embodiments, the lead anchor can include a coating, sleeve, or jacket. A coating, sleeve, or jacket may include one or more materials selected to resist or prevent damage or irritation to patient tissue. For example, a coating, sleeve, or jacket of a lead anchor 450 may be composed of one or more materials that are softer, more pliable, or smoother than the material forming the first layer. For example, in at least some embodiments, the first layer of the anchor body 452 is formed from a metal or alloy, such as, for example, stainless steel, and a coating, sleeve, or jacket is formed of silicone, latex, or the like; or any combination thereof.

The lead anchor 450 defines one or more lead channels 454, 456. The illustrated anchor body 452 defines two lead channels 454, 456 therein. In at least some other embodiments, the anchor body may define one, three, four, five, six, seven, eight, or more lead channels. Each lead channel 454, 456 can receive at least one lead 480, 490. For example, FIG. 4A shows a single lead 480, 490 disposed in each of the lead channels 454, 456. In at least some other embodiments, a lead channel 454, 456 may be configured and arranged to receive two, three, four, or more leads, depending on, for example, the arrangement of the lead anchor 450, the needs of the patient and nature of the procedure, or any combination thereof.

A variety of different shapes of a lead channel 454, 456 can be suitable for receiving a lead. Any suitable cross-sectional shape of a lead channel 454, 456, can be selected and may be chosen depending on one or more factors, including, for example, the size, shape, or number of leads 480, 490 to be received, or any combination thereof. Each of the illustrated lead channels 454, 456 in FIGS. 4A-4C has a "U"-shaped cross section. In at least some other embodiments, a lead channel 454, 456 may define a cross-section having a round shape, an oblong shape, a triangular shape, a trapezoidal shape, or another shape. In at least some embodiments, all of the lead channels 454, 456 of the lead anchor 450 define the same cross-sectional shape. In at least some other embodiments, at least one lead channel defines a cross-sectional shape that is different from the cross-sectional shape of at least one other lead channel.

As described above, a lead channel, 454, 456 may be open or closed along the front surface 452c. Where the lead channels 454, 456 are defined along an open surface (e.g., front surface 452c in FIG. 4C) of the anchor body 452. In at least some embodiments, one or more of the lead channels 454, 456 defines a lip along the front surface 452c that the lead 480, 490 can be pushed past when the lead is received by the lead anchor 450, but that resists withdrawal of the lead from the lead channel.

The anchor body 452 can have any size or shape and selection of the size or shape may be based on one or more factors such as, for example, the implantation site of the lead 480, 490 or lead anchor 450, the anatomy of the patient, the number, size, and shape of leads to be anchored, or the nature of the procedure, or any combination thereof. In at least some embodiments, the anchor body 452 includes at least one suture channel formed along an outer surface of the anchor body. The suture channel can receive a suture that extends around the lead anchor 450 to fix the lead anchor to patient tissue. Additionally or alternatively, the lead anchor 450 may be attached to patient tissue by, for example, a staple, an adhesive, or any other suitable attachment device, material, or method.

In at least some embodiments, the anchor body 452 has at least two lateral portions 452g, 452i (FIG. 5A) and at least one medial portion 452h (FIG. 5A). In at least some embodiments, both of the lead channels 454, 456 assume a sigmoidal path curving inwardly relative to the lateral portions 452g, 452i toward the medial portion 452h while extending longitudinally along the anchor body 452.

In other situations involving multiple leads, it may be advantageous for two or more of the leads 480, 490 to be further spaced apart upon exiting the lead anchor 450.

Therefore, it may be desirable for each lead channel 454, 456 to assume a path with a shallower inward curve than is shown in FIG. 4A or, alternatively, a path that curves from a medial portion 452h outwardly toward a lateral portion 452g, 452i in order to create additional space between the leads 480, 490 at the second end 452b of the anchor body 452. In at least some embodiments, the lead channels 454, 456 do not cross one another. In at least in some embodiments, the lead channels have parallel pathways or mirror-image pathways (as illustrated in FIGS. 4A-5B).

A variety of different paths can be used to form non-linear lead channels (for example, curved or undulating lead channels.) For example, in at least some embodiments, the lead channels 454, 456 are nonlinear lead channels having a straight section, followed by a curve, and then another straight section as they travel from the first end 452a to the second end 452b of the anchor body 452. In at least some embodiments, the lead channels 454, 456 are nonlinear lead channels that assume mirroring paths with a sigmoidal curve to permit efficient installation and anchoring of both leads 480, 490 within the lead anchor 450.

The lead anchor 450 also includes a wedge element 460 for engaging and anchoring the leads 480, 490. The wedge element 460 is operably connected to an actuator 470. The wedge element 460 travels, in response to the actuator 470, between an open position (see FIGS. 4A, 4B and 5A) and an engagement position (see FIGS. 4D and 5B) within the anchor body 452. To travel from the open position to the engagement position, the wedge element 160 is moved by the actuator 470 toward the second end 452b of the anchor body 452 in the same longitudinal direction as the lead channels 454, 456. When the wedge element 460 is in an open position, the leads 480, 490 may slide relative to, or be released from, the lead anchor 450. In an engagement position, the wedge element 160 anchors one or more leads 480, 490 in the lead anchor 450 by engaging the leads and, at least in some embodiments, compressing the leads against a wall of the lead channels 454, 456

The wedge element 460 is coupled to the actuator 470. In at least some embodiments, the wedge element 460 is "C"-shaped as illustrated in FIG. 4A. The minor, or inner, curved surface 462 (FIG. 4C) of the wedge element 460 receives the actuator 470. The major, or outer, curved surface 464 (FIG. 4C) engages the leads 480, 490 in the lead channels 454, 456 when wedge element 460 is in an engagement position. It will be understood that at least a portion of the wedge element 460 may have any other suitable shape or construction. For example, in at least some embodiments, the engaging surface 460 of the wedge 460 has a round or arced shape. In other embodiments, at least a portion of the wedge element 460 has an oblong shape, or a polygonal shape, such as a triangular shape, a pyramidal shape, a rhomboid shape, an arrowhead shape, or another shape suitable for engaging a lead 480, 490 and anchoring the lead in a lead channel 454, 456.

Figure 7A:
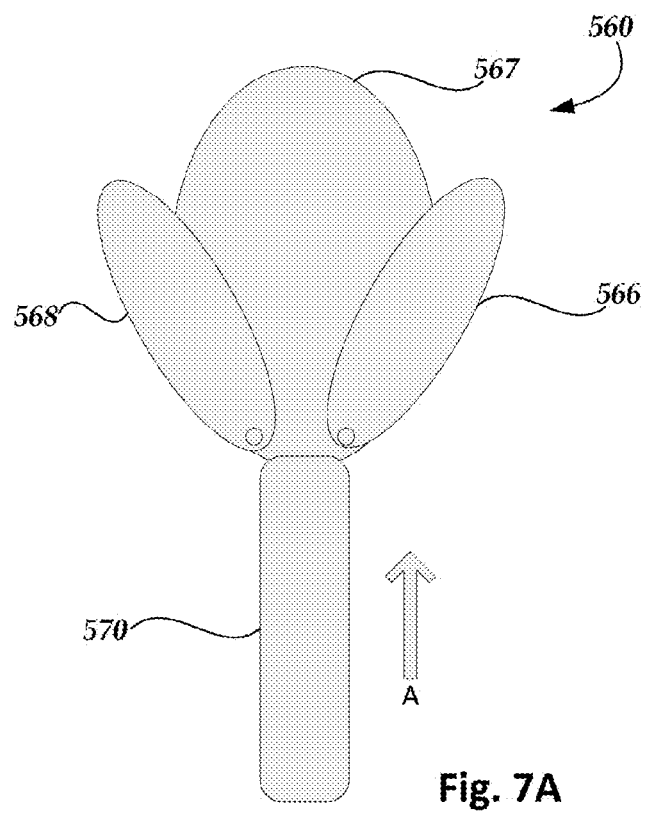
FIG. 7A is a schematic top plan view of another embodiment of an actuator and a wedge element including a pivotable arm with the wedge element in an open position, according to present invention.
Figure 7B:
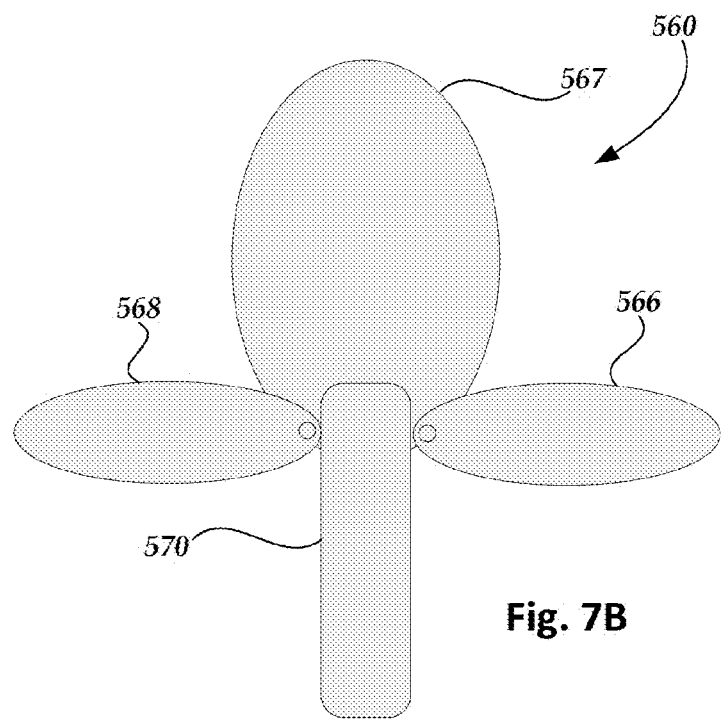
FIG. 7B is a schematic top plan view of the actuator and the wedge element of FIG. 7A with the wedge element is in an engagement position, according to the invention.

In other embodiments, the wedge element 560 includes at least one pivotable arm 566, 568, as illustrated in FIGS. 7A and 7B, movable in response to the actuator 570 from the open position to the engagement position to anchor a lead. The pivotable arms 566, 568 can be nested close to a wedge body 567, as illustrated in FIG. 7A, and constrained by, for example, walls of the medial section 452h (FIG. 5A) when the wedge element 560 is in the open position. The wedge element 560 is moved into the engagement position by advancing the actuator 570 in, for example, the direction of Arrow A in FIG. 7A. The pivotable arms 566, 568 can then be released, as illustrated in FIG. 7B, to engage the leads when the wedge element is in the engagement position. In still other embodiments, movement of the actuator may release the arms 566, 568 of the wedge element 560 by spring action. Preferably, the wedge element 460, 560 is shaped to resist or prevent damage to the leads 480, 490 (for example, the wedge element does not have sharp edges that might puncture or crimp the lead).

Figure 4B:
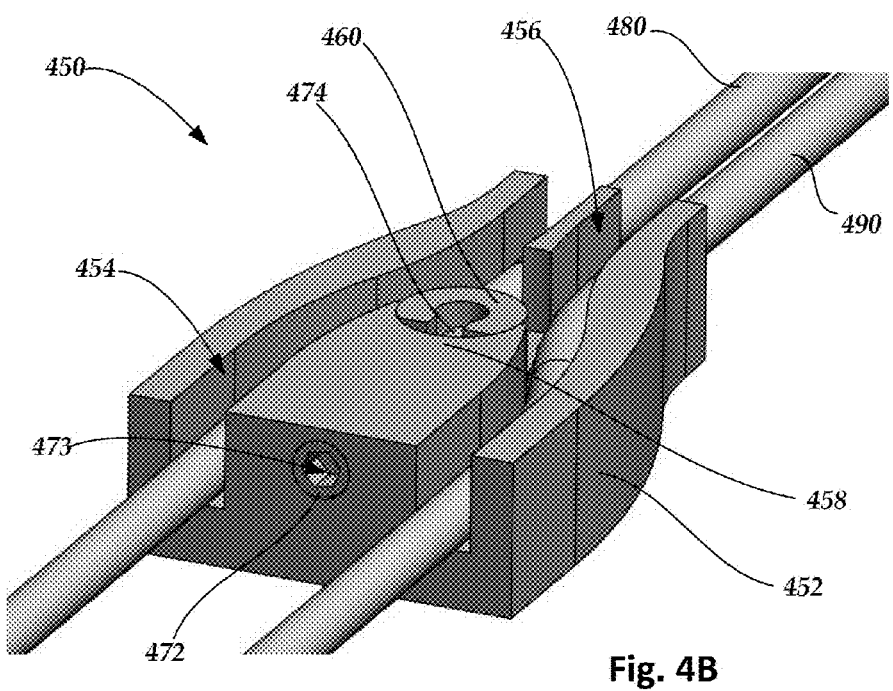
FIG. 4B is a schematic perspective view of the lead anchor of FIG. 4A showing the first end of the lead anchor, according to the invention.
Figure 4C:
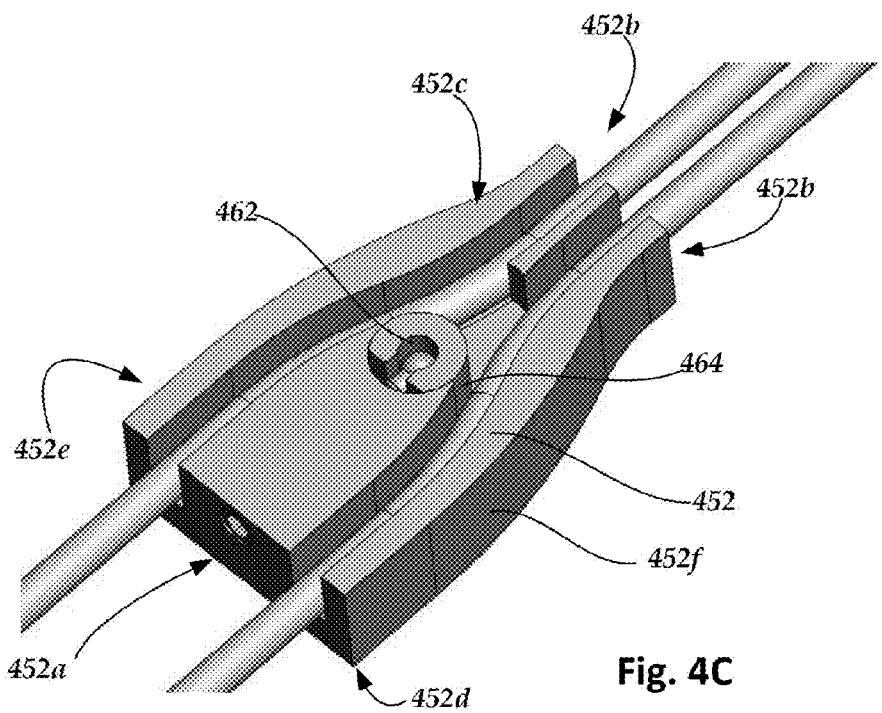
FIG. 4C is a schematic perspective view of the lead anchor of FIG. 4A with the wedge element in an open position, according to the invention.
Figure 4D:
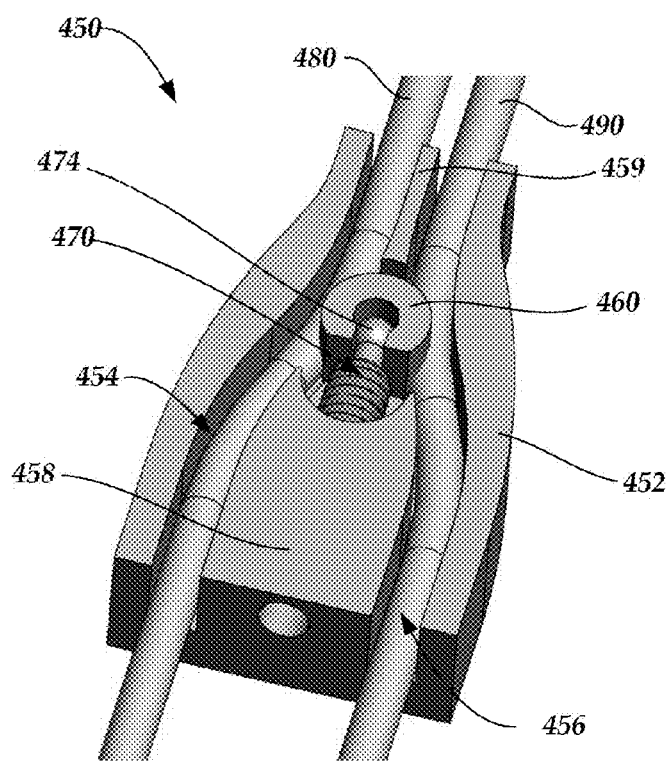
FIG. 4D is a schematic perspective view of the lead anchor of FIG. 4A with the wedge element in an engagement position, according to the invention.

In at least some embodiments, the lead anchor 450 has a single wedge element 460 and a single actuator 470. Alternatively, the lead anchor 450 may include multiple wedge elements 460 attached to a single actuator or multiple actuators 470, each actuator being operatively connected to one or more of the wedge elements.

Where the anchor body 452 defines multiple lead channels, there may be a corresponding channel divider, such as the medial divider 459, between at least a portion of each two adjacent lead channels 454, 456. As illustrated in FIG. 4D, lead channels 454, 456 that come into close proximity may allow a single wedge element 460 to anchor leads 480, 490 in at least two channels.

Any suitable actuator 470 can be used for moving the wedge element 460 toward the second end 452b from the open position to the engagement position. In at least some embodiments, the actuator 470 is rotatable to move the wedge element 460 between the open position and the engagement position. In at least some embodiments, the actuator 470 includes a screw having a head 472 (see, e.g., FIG. 4B) and a tip 474 (see, e.g., FIG. 4D). The tip 474 engages the wedge element 460. In at least some embodiments, the tip 474 may define a ball-shaped engaging end for engaging the inner, or minor, curve 462 of a C-shaped wedge element 460. It will be appreciated that the tip 474 may define, or may alternatively be coupled to, a separate engaging end having a shape suitable for operably engaging the corresponding wedge element 460.

In at least some other embodiments, the actuator 470 assumes a configuration other than a screw, such as, for example, a pin that is configured and arranged to be pushed, pulled, or pushed and pulled along a portion of the anchor body 452. In at least some embodiments, the actuator 470 includes a pin and one or more of the lead channel 454, 456 and the anchor body 452 defines a detent or other element that resists or prevents unintended reverse travel of the wedge element 460 from the engagement position toward the open position.

In at least some embodiments having an actuator 470 with a head 472, the head 472 is adapted to be engaged by a clinician for moving the actuator 470 and, by extension, the wedge element 460. As illustrated in FIG. 4B, the head 472 of the actuator 470 may define a hexagonal recess 473 adapted for engagement by a hexagonal tool, such as, for example, an Allen wrench. When so engaged, the head 472 may be rotated, turning the actuator 470 and moving the wedge element 460. It will be understood that the head 472 may adapt any suitable configuration for engaging a turning tool. For example, in at least some "turning" embodiments, the head 472 may be a slot head, a clutch head, a socket head, a Philips head, a spline head, or a tri-wing head, among other configurations known to those of skill in the art. In at least some other embodiments having a head 472, the head can receive a pulling or pushing tool to operate the actuator 470.

In at least some embodiments, the actuator 470 is disposed within an actuator housing 458 defined, or, alternatively, disposed, along a portion of the anchor body 452. As illustrated in FIG. 5A, the actuator housing 458 is defined along a medial portion (e.g., 452h) of the anchor body 452. The actuator housing 458 receives the actuator 470. The head 472 of the actuator 470 is disposed along, and is accessible from, the first end of the actuator housing 458 (in at least some embodiments, the first end of the housing 458 is defined along or aligns with the first end 452a of the anchor body 452), while the tip 474 of the actuator 470 protrudes from the second end of the actuator housing 458.

The actuator housing 458 may assume any configuration appropriate to receive the wedge element 460 or to provide a resting surface therefor when the wedge element 460 is in the fully open position. For example, it at least some embodiments, the second end of the housing 458 is recessed to receive the wedge element 460 when the wedge element 460 is in the fully open position. The actuator housing 458 may further partially define at least one lead channel 454, 456. For example, in the illustrated embodiment, the actuator housing 458 separates the lead channels 454, 456.

In at least some embodiments, the actuator 470 is disposed along the first end 452a of the anchor body 452. In at least some other embodiments, the actuator 470 is disposed along the second end 452b of the anchor body 452 and the fully open position of the wedge element 460 is located toward the first end 452a of the anchor body 452. In such embodiments, moving the wedge element 460 to an engagement position may involve moving the actuator 470 in a reverse direction away from the second end 425b of the anchor body 452. It will be appreciated that in embodiments having an actuator housing 458, the housing 458 is defined or, alternatively, disposed along the same end of the anchor body 452 as the actuator 470.

Movement of the wedge element 460 from an open position to an engagement position is illustrated in, for example, FIGS. 5A and 5B. In FIG. 5A, the wedge element 460 is in an open position and is docked against the actuator housing 458. When in an open position, wedge element 460 does not engage or compress the leads 480, 490 and the leads may be removed from or come free of the lead channels 454, 456. In an engagement position (see FIG. 5B), the wedge element 460 engages and, in some embodiments, compresses the leads 480, 490 to anchor the leads in the lead channels 454, 456.

In at least some embodiments, the actuator 470 can reversibly move the wedge element 460 between open and engagement positions. In at least some other embodiments, the actuator 470 can move the wedge element 460 only from an open position to an engagement position.

A kit can be provided that includes a lead and one or more of the lead anchors described above. The kit may also include a control module coupleable to the lead.

Figure 8:
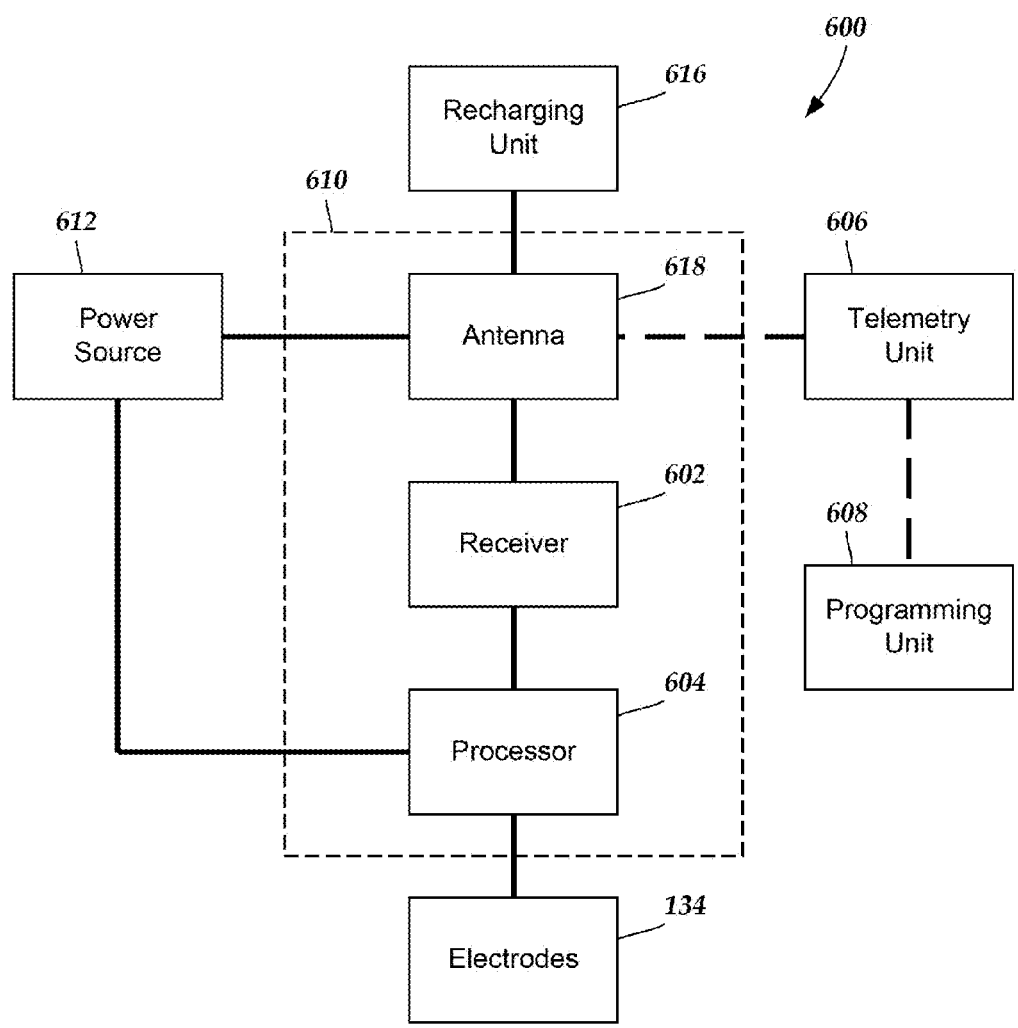
FIG. 8 is a schematic overview of one embodiment of components of a stimulation system, including an electronic subassembly disposed within a control module, according to the invention.

FIG. 8 is a schematic overview of one embodiment of components of an electrical stimulation system 600 including an electronic subassembly 610 disposed within a control module. It will be understood that the electrical stimulation system can include more, fewer, or different components and can have a variety of different configurations including those configurations disclosed in the stimulator references cited herein.

Some of the components (for example, a power source 612, an antenna 618, a receiver 602, and a processor 604) of the electrical stimulation system can be positioned on one or more circuit boards or similar carriers within a sealed housing of an implantable pulse generator, if desired. Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 616 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 604 is generally included to control the timing and electrical characteristics of the electrical stimulation system. For example, the processor 604 can, if desired, control one or more of the timing, frequency, strength, duration, and waveform of the pulses. In addition, the processor 604 can select which electrodes can be used to provide stimulation, if desired. In some embodiments, the processor 604 selects which electrode(s) are cathodes and which electrode(s) are anodes. In some embodiments, the processor 604 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 608 that, for example, allows modification of pulse characteristics. In the illustrated embodiment, the processor 604 is coupled to a receiver 602 which, in turn, is coupled to the optional antenna 618. This allows the processor 604 to receive instructions from an external source to, for example, direct the pulse characteristics and the selection of electrodes, if desired.

In one embodiment, the antenna 618 is capable of receiving signals (e.g., RF signals) from an external telemetry unit 606 which is programmed by the programming unit 508. The programming unit 608 can be external to, or part of, the telemetry unit 506. The telemetry unit 606 can be a device that is worn on the skin of the user or can be carried by the user and can have a form similar to a pager, cellular phone, or remote control, if desired. As another alternative, the telemetry unit 506 may not be worn or carried by the user but may only be available at a home station or at a clinician's office. The programming unit 608 can be any unit that can provide information to the telemetry unit 606 for transmission to the electrical stimulation system 600. The programming unit 608 can be part of the telemetry unit 606 or can provide signals or information to the telemetry unit 606 via a wireless or wired connection. One example of a suitable programming unit is a computer operated by the user or clinician to send signals to the telemetry unit 606.

The signals sent to the processor 604 via the antenna 618 and the receiver 602 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 600 to cease operation, to start operation, to start charging the battery, or to stop charging the battery. In other embodiments, the stimulation system does not include the antenna 618 or receiver 602 and the processor 604 operates as programmed.

Optionally, the electrical stimulation system 600 may include a transmitter (not shown) coupled to the processor 604 and the antenna 618 for transmitting signals back to the telemetry unit 606 or another unit capable of receiving the signals. For example, the electrical stimulation system 600 may transmit signals indicating whether the electrical stimulation system 600 is operating properly or not or indicating when the battery needs to be charged or the level of charge remaining in the battery. The processor 604 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor, comprising:
   an anchor body having a first end and a second end opposite the first end, the anchor body defining at least one lead channel extending longitudinally from the first end to the second end;
   a wedge element disposed adjacent to at least a portion of the at least one lead channel, the wedge element configured and arranged to move between an open position and an engagement position; and
   an actuator configured and arranged to move the wedge element towards the second end from the open position to the engagement position;
   wherein in the engagement position, the wedge element engages a lead disposed in the at least one lead channel to hold the lead within the lead anchor; and
   wherein in the open position, the wedge releases the lead to move relative to or be released from the lead anchor.

2. The lead anchor of claim 1, wherein the at least one lead channel comprises two nonlinear lead channels extending longitudinally from the first end to the second end.

3. The lead anchor of claim 2, wherein the two nonlinear lead channels are mirror images of each other.

4. The lead anchor of claim 1, wherein each of the at least one lead channel comprises a curved portion.

5. The lead anchor of claim 1, wherein the actuator is rotatable to move the wedge element from the open position to the engagement position.

6. The lead anchor of claim 5, wherein the actuator is a screw.

7. The lead anchor of claim 1, wherein the actuator comprises a pin.

8. The lead anchor of claim 1, wherein the actuator is configured and arranged to reversibly move the wedge element between the open position and the engagement position.

9. The lead anchor of claim 1, wherein the at least one lead channel is open along one surface of the anchor body to permit side loading of at least one lead into the lead anchor.

10. The lead anchor of claim 1, wherein the wedge element is C-shaped.

11. The lead anchor of claim 1, wherein the wedge element has an oblong shape or polygonal shape.

12. The lead anchor of claim 1, wherein the wedge element comprises at least one pivotable arm.

13. A kit, comprising:
    at least one electrostimulation lead; and
    the lead anchor of claim 1 configured and arranged for receiving the at least one electrostimulation lead in the at least one lead channel of the lead anchor.

14. The kit of claim 13, further comprising a control module.

15. A method of anchoring at least one electrostimulation lead, the method comprising:
    inserting a first electrostimulation lead into the at least one lead channel of the lead anchor of claim 1 with the wedge element in the open position; and moving the wedge element towards the second end from the open position to the engagement position using the actuator to anchor the lead to the lead anchor.

16. The method of claim 15, wherein the at least one lead channel comprises two nonlinear lead channels extending longitudinally from the first end to the second end, the method further comprising inserting a second electrostimulation lead into a different one of the at least one lead channel of the lead anchor with the wedge element in the open position.

17. The method of claim 15, further comprising attaching the lead anchor to patient tissue.

18. The method of claim 15, wherein inserting a first electrostimulation lead comprises side loading the first electrostimulation lead into the at least one lead channel of the lead anchor.

19. The method of claim 15, wherein inserting a first electrostimulation lead comprises end loading the first electrostimulation lead into the at least one lead channel of the lead anchor.

20. The method of claim 15, further comprising coupling the first electrostimulation lead to a control module.

* * * * *